US009475786B2

(12) United States Patent
Ibert et al.

(10) Patent No.: US 9,475,786 B2
(45) Date of Patent: Oct. 25, 2016

(54) METHOD FOR SYNTHESISING 2,5-DI(HYDROXYMETHYL)FURAN AND 2,5-DI(HYDROXYMETHYL) TETRAHYDROFURAN BY SELECTIVE HYDROGENATION OF FURAN-2,5-DIALDEHYDE

(71) Applicant: ROQUETTE FRERES, Lestrem (FR)

(72) Inventors: Mathias Ibert, La Chappelle d'Armentieres (FR); Flora Chambon, Marc En Baroeul (FR); Laurent Dambrine, Sains en Gohelle (FR)

(73) Assignee: ROQUETTE FRERES, Lestrem (FR)

( * ) Notice: Subject to any disclaimer, the term of this patent is extended or adjusted under 35 U.S.C. 154(b) by 0 days.

(21) Appl. No.: 14/431,571

(22) PCT Filed: Sep. 26, 2013

(86) PCT No.: PCT/FR2013/052272
§ 371 (c)(1),
(2) Date: Mar. 26, 2015

(87) PCT Pub. No.: WO2014/049275
PCT Pub. Date: Apr. 3, 2014

(65) Prior Publication Data
US 2015/0252015 A1  Sep. 10, 2015

(30) Foreign Application Priority Data
Sep. 27, 2012  (FR) ...................................... 12 59102

(51) Int. Cl.
*C07D 307/42*  (2006.01)
*C07D 307/40*  (2006.01)
*C07D 307/12*  (2006.01)

(52) U.S. Cl.
CPC .......... *C07D 307/42* (2013.01); *C07D 307/12* (2013.01); *C07D 307/40* (2013.01)

(58) Field of Classification Search
CPC . C07D 307/42; C07D 307/40; C07D 307/12
See application file for complete search history.

(56) References Cited

U.S. PATENT DOCUMENTS

| 7,317,116 | B2 | 1/2008 | Sanborn |
| 2011/0306780 | A1 | 12/2011 | Lilga et al. |
| 2014/0378691 | A1 | 12/2014 | Dambrine et al. |

FOREIGN PATENT DOCUMENTS

| FR | 1162343 A | | 11/1956 |
| WO | WO 2006/063287 | * | 6/2006 |
| WO | 2007/146836 A1 | | 12/2007 |
| WO | 2008/053284 A1 | | 5/2008 |
| WO | 2012/082665 A1 | | 6/2012 |

OTHER PUBLICATIONS

Yuskovets, Z.G.,"Reduction of aldehydes of the furan series by the method of catalytic hydrogen transfer." Chemistry of Heterocyclic Compounds 26.6 (1990): 620-624.*
Partenheimer, W., "Synthesis of 2, 5-Diformylfuran and Furan-2, 5-Dicarboxylic Acid by Catalytic Air-Oxidation of 5-Hydroxymethylfurfural. Unexpectedly Selective Aerobic Oxidation of Benzyl Alcohol to Benzaldehyde with Metal=Bromide Catalysts." Advanced Synthesis & Catalysis 343.1 (2001): 102-111.*
Schiavo V et al.: "Catalytic hydrogenation of 5-(hydroxymethyl)furfural in aqueous medium", Bulletin De La Societe Chimique De France, Societe Francaise De Chimie. Paris, France, Jan. 1, 1991, pp. 704-711, XP008085941, ISSN: 0037-8968 cited in the application the whole document p. 706, col. 1, line 5-line 11.
Yoshinao Nakagawa et al. "Total hydrogenation of furan derivatives over silica-supported Ni-Pd alloy catalyst", Catalysis Communications. Elsevier Science. Amsterdam. NL. vol. 12. No. 3. Sep. 2, 2010. pp. 154-156. XP028152982, ISSN: 1566-7367. DOI: 10.1016/J.CATCOM.2010.09.003 [retrieved on Sep. 15, 2010] cited in the application the whole document p. 155. col. 2. line 8-line 9.
Tong et al.: "Biomass into chemicals: Conversion of sugars to furan derivatives by catalytic processes", Applied Catalysis A: General 385 (2010) 1-13, Applied Catalysis A: General, Tianjin Key Laboratory of Catalysis Science and Technology and State Key Laboratory for Chemical Engineering (Tianjin University). School of Chemical Engineering. Tianjin University. Tianjin 300072. China.
International Search Report, dated Nov. 12, 2013, from corresponding PCT application.

* cited by examiner

*Primary Examiner* — Samantha Shterengarts
*Assistant Examiner* — Matt Mauro
(74) *Attorney, Agent, or Firm* — Young & Thompson

(57) ABSTRACT

A method for selective hydrogenation of furan-2,5-dialdehyde (DFF) into 2,5-di(hydroxymethyl)furan (DHMF) and into 2,5-di(hydroxymethyl)tetrahydrofuran (DHMTHF). In relation to the prior art, which uses C6 sugars or 5-hydroxymethyl furaldehyde (5-HMF) as raw materials, the method can be performed at low temperatures (lower than 120° C., preferably 80° C.), while consuming low amounts of catalyst relative to the initial reagent (in particular less than 5%, preferably less than 2% relative to the weight of the reagent). The heterogeneous catalyst used can also be recycled from one reaction to another. Finally, the choice of experimental conditions enables the selective formation of DHMF or DHMTHF.

10 Claims, No Drawings

METHOD FOR SYNTHESISING 2,5-DI(HYDROXYMETHYL)FURAN AND 2,5-DI(HYDROXYMETHYL) TETRAHYDROFURAN BY SELECTIVE HYDROGENATION OF FURAN-2,5-DIALDEHYDE

The present invention relates to a process for the selective hydrogenation of furan-2,5-dialdehyde (DFF) to give 2,5-di(hydroxymethyl)furan (DHMF) and 2,5-di(hydroxymethyl)-tetrahydrofuran (DHMTHF). Quite advantageously with respect to the prior art which uses C6 sugars or 5-hydroxymethyl furaldehyde (5-HMF) as initial raw materials, the process according to the present invention takes place at low temperatures (preferably between 30° C. and 120° C.), while using a small amount of catalyst with respect to the initial reactant (preferably less than 2% with respect to the weight of the reactant).

While avoiding technical constraints linked to the use of high temperatures, the Applicant has therefore developed an economically advantageous process by reducing the amount of catalyst used, allowing the selective synthesis of DHMF and DHMTHF, while exploring a new DFF-based pathway for attaining these compounds.

There has been considerable development in the chemistry of furan and its derivatives over the last few years. Among the furan compounds of significance, mention may especially be made of 2,5-di(hydroxymethyl)furan (DHMF) and 2,5-di(hydroxymethyl)-tetrahydrofuran (DHMTHF) which find applications in adhesives, seals, composites, coatings, foams and solvents or else as synthetic intermediates for the manufacture of polymers, these applications being disclosed in document US 2011/306780. The specific use of DHMF in the production of polyurethane foams and polyesters is itself reported in the document "Biomass into chemicals: Conversion of sugars to furan derivatives by catalytic processes" (Applied Catalysis A: General 285, pp.1-13, 2010).

2,5-Di(hydroxymethyl)furan (DHMF) and 2,5-di(hydroxymethyl)tetrahydrofuran (DHMTHF) correspond to the following formulae :

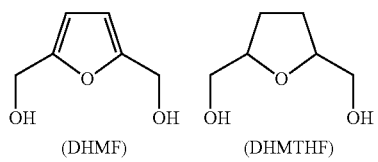

(DHMF)    (DHMTHF)

There are 2 pathways that lead to the production of these products:
the catalytic hydrogenation of 5-hydroxymethyl furaldehyde (5-HMF) or
the tandem (or bifunctional) catalysis that consists in dehydrating and then hydrogenating C6 sugars.

In the first category, mention may be made of document "Total hydrogenation of furan derivatives over silica-supported Ni-Pd alloy catalyst" (Catal. Comm., 12, pp. 154-156, 2010) which discloses the synthesis of DHMTHF from 5-HMF dissolved in water and methanol, in the presence of a nickel-palladium bimetallic catalyst supported on silica. The reaction takes place over 2 hours at 40 degrees, with a degree of conversion of the reactant of 99 mol % and a yield in moles of 96% DHMTHF. However, the amount of catalyst used is large since it is equal to 16% of the total weight of 5-HMF used.

Reference may also be made to document U.S. Pat. No. 7,317,116 which describes the synthesis of DHMF starting from 5-HMF. The latter is dissolved in methanol and the reaction is catalyzed by nickel. The conversion is complete and a yield of greater than 90 mol % DHMF is obtained. Nevertheless, a significant amount of catalyst is consumed (6.7% with respect to the weight of 5-HMF) and it is necessary to work at high temperature (150° C.).

Document WO 2007/146836 describes the synthesis, in water, of DHMF, with a bulk catalyst of Raney cobalt type. The synthesis is then carried out at 60° C. for a complete conversion of the 5-HMF and a yield of 97 mol % of final product. It should be emphasised that a very large amount of catalyst is used here: this catalyst represents 51% by weight of the initial 5-HMF.

Lastly, the document "Hydrogenation of 5-hydroxymethylfurfural, in aqueous medium" (Bull. Soc. Chim. Fr., 1991, 128, pp. 704-711) presents the synthesis of DHMF and DHMTHF with respective yields, in moles, of 100% and 92%, with different bulk catalysts used in an amount of around 10% with respect to the weight of 5-HMF, and at a temperature of 140° C.

The other method of synthesizing DHMF and DHMTHF consists in dehydrating, then catalytically hydrogenating C6 sugars. In this regard, mention may be made of document WO 2008/053284 which describes the hydrogenation of glucose in the presence of a palladium-on-carbon catalyst, in a proportion of the order of 3% with respect to the weight of reactant. However, it is necessary to work at 130° C. in order to obtain a degree of conversion of 90% with respect to the glucose and a yield of 90 mol % DHMF.

In this same category, mention may lastly be made of document WO 2012/082665 which focuses on fructose as initial raw material. The amounts of catalyst vary between 3% and 33% with respect to the weight of fructose. No information is given regarding the yields and the degrees of conversion; it appears on the other hand that it is necessary to work at 130° C., or even at 180° C.

Consequently, the prior art processes that aim to obtain DHMF and/or DHMTHF from 5-HMF or from C6 sugars have the drawback of using high temperatures (need for systems for heating and insulating the plants, for control of the cooling conditions, and dangerousness for the user) and/or of consuming large amounts of catalyst with respect to the mass of the initial reactant (processes that are not very profitable economically, especially considering the price of the catalyst).

Working to overcome these drawbacks, the Applicant has successfully developed a novel process for synthesizing DHMF and DHMTHF. This process is based on the selective hydrogenation of DFF, a raw material never before envisaged for the synthesis of the aforementioned compounds. Very advantageously, this process makes it possible to work at relatively low temperatures, in particular preferably between 30° C. and 120° C. Furthermore, the amounts of catalyst used remain very low with respect to the initial DFF: they are less than 5% of the weight of said DFF.

Another advantage of the process developed by the Applicant lies in the possibility of obtaining the preferential formation of DHMF or DHMTHF depending on the experimental conditions. The initial reactant is therefore a composition containing DFF, which means that said composition may contain a compound other than DFF. Advantageously, the composition containing DFF has a very high content of DFF; it contains said DFF in a proportion by weight at least equal to 90%, preferably 95%, very preferably 98%. Quite advantageously, the composition containing DFF in the aforementioned proportions is derived from the oxidation of 5-HMF according to the process that is the subject of the French patent application having the filing number 1162343. This application describes a process that makes it possible to very easily obtain a composition having a high content of DFF from 5-HMF, the initial 5-HMF not necessarily having a high degree of purity. In comparison, the processs for producing DHMF and DHMTHF from 5-HMF in general require a very high degree of purity of 5-HMF.

In the initial DFF composition, the residual product is in general FFCA (5-furaldehyde-2-carboxylic acid) resulting from the process that is the subject of the aforementioned patent application. The initial composition then preferably contains at least 90% by weight of DFF, preferably at least 95% by weight of DFF, more preferably 99% by weight of DFF, the FFCA representing in each of these cases the remainder of the composition.

Thus, a first subject of the present invention consists of a process for synthesizing DHMF and/or DHMTHF, by bringing into contact:
a) a composition containing DFF at a high content (>90%),
b) a protic solvent,
c) a source of hydrogen,
d) and a hydrogenation catalyst.

Throughout the present application, the terms selectivity (S), conversion (C) and yield (Y) are used with reference to the following definitions:
C (mol %)=((amount of DFF converted)×100)/initial amount of DFF
S=(amount of DHMF or of DHMTHF formed)/amount of DFF converted
Y (mol %)=S×C/100

The process that is the subject of the aforementioned patent application no. 1162343 is characterized in that it comprises a step of oxidation of 5-HMF in the presence of at least an organic acid, a nitroxyl radical, a source of oxygen and an oxygen transfer agent. The nitroxyl radical is in particular chosen from (2,2,6,6-tetramethylpiperidin-1-yl) oxy radicals, also referred to as TEMPO radicals.

The protic solvent used in the present invention is more specifically selected from water, methanol, ethanol, isopropanol, 1-propanol, 1-butanol and the mixtures of these solvents, water being the preferred solvent.

The synthesis reaction via hydrogenation takes place at a temperature between 30° C. and 180° C., preferably between 30° C. and 150° C., more preferably between 50° C. and 120° C.

The source of hydrogen is selected from all sources available to a person skilled in the art. Preferably, it is molecular hydrogen, which is generally stored in pressurized containers. The hydrogen may also be extracted from "hydrogen donors", which are often solvents such as hydrazine, dihydronaphthalene, dihydroanthracene, isopropanol, methanoic acid, or else cyclohexadiene. When it is molecular hydrogen, this is under a pressure of between 1 bar and 400 bar, preferably between 10 bar and 110 bar.

The hydrogenation catalyst is selected from heterogeneous catalysts well known to a person skilled in the art, and in particular from conventional metal catalysts for hydrogenation. The catalyst is of bulk or supported type. In the first case, it is preferably a catalyst based on a Raney metal. In the second case, the support is selected from activated carbon, silica, alumina, mixtures of silica and alumina, oxides of titanium, zirconium, magnesium and cerium, mixed oxides based on Si, Al, Ti and Zr. In this case, the metal content represents from 0.1% to 90% of the total weight of the catalyst. In all cases, the catalyst is based on Ni, Cu, Fe, Pd, Rh, Ir, Ru, Co, Pt, and more preferably based on Ni and Pd.

The contact time between the various constituents a), b), c) and d) is between 1 minute and 8 hours, preferably between 15 minutes and 2 hours.

As for the rest, the hydrogenation process of the present invention may be carried out in any type of fixed bed or batch reactor that is pressurized or unpressurized, preferably pressurized. The type of batch reactor may be an autoclave provided with a variable speed agitator. Preferably, the reactor is additionally provided with a gas inlet tube, connected to a pressurized system provided with a pressure-reducing valve and with a gas discharge tube. The reactor may additionally comprise a cooling system and also a system for measuring and regulating the temperature. Within the context of a batch reactor, the amount of catalyst is between 0.01% and 30%, more preferably between 0.1% and 5%, very preferably between 0.15% and 2.5% with respect to the weight of the DFF composition.

During the hydrogenation process, the reaction medium is kept stirring. The stirring speed is preferably set at between 800 and 2200 rpm, more preferably between 1500 and 1700 rpm.

The process according to the invention may additionally comprise a step of filtering the reaction medium resulting from the hydrogenation step, thus making it possible to separate the DHMF and/or DHMTHF reaction product(s) from the solid catalyst.

Owing in particular to the high DFF content of the initial composition, the catalyst used in the present invention can easily be recycled. The Applicant has even been able to observe, during the experiments that it carried out, that the activity of the catalyst was not modified, even when said catalyst had been recycled 5 times.

The following examples make it possible to better understand the present invention, without however limiting the scope thereof.

EXAMPLES

Example of the Synthesis of DHMTHF in the Presence of the Palladium-on-carbon Catalyst In this test, use is made of:
a composition containing DFF (93.1% by weight of DFF and 6.9% by weight of FFCA): 9 g;
a Pd/C palladium-on-carbon catalyst in an amount of 0.2% by weight of Pd with respect to the weight of DFF;
demineralized water: 420 ml.
Operating conditions:
reaction temperature: 120° C.;
initial pH of the reaction: 5.5;
hydrogen pressure: 50 bar;
reaction time: 1 h 15 min.

Introduced into a stainless steel autoclave having an internal capacity of 600 ml are: 9 g of a composition containing DFF, and the Pd/C commercial catalyst and also 420 ml of demineralized water. The pH of the reaction medium is adjusted to 5.5. When all the reactants have been placed in the autoclave, the latter is purged under nitrogen, then placed under 50 bar of hydrogen at the start of the heating while stirring (1600 rpm). From 70° C. onwards, a consumption of hydrogen is observed, indicating the start of the hydrogenation reaction. After a contact time of 1 h 15 min, the autoclave is cooled using the cooling coil and by cutting the heating. The stirring is reduced to 250 rpm during the cooling. When the reactor reaches 30° C., the stirring is stopped and the autoclave is depressurized. The autoclave is opened and the reaction medium obtained is filtered through an 8 μm Millipore filter in order to separate the reaction medium from the solid catalyst, which can be reused in another hydrogenation reaction. A sample of the crude reaction product is withdrawn then analyzed by gas chromatography.

A conversion of 100% is observed with a DHMTHF selectivity of 79%. This test corresponds to test no. 10 in table 1.

Example of the Synthesis of DHMF in the Presence of the Palladium-on-carbon Catalyst In this test, use is made of:
a composition containing DFF (99.2% by weight of DFF and 0.8% by weight of FFCA): 10 g;
a Pd/C palladium-on-carbon catalyst in an amount of 0.2% by weight of Pd with respect to the weight of DFF;
demineralized water: 400 ml.
Operating conditions:
reaction temperature: 70° C.;
initial pH of the reaction: 5;
hydrogen pressure: 20 bar;
reaction time: 1 h 30 min.

Introduced into a stainless steel autoclave having an internal capacity of 600 ml are: 10 g of a composition containing DFF, and the Pd/C catalyst and also 400 ml of demineralized water. The pH of the reaction medium is adjusted to 5. When all the reactants have been placed in the autoclave, the latter is purged under nitrogen, then placed under 20 bar of hydrogen at the start of the heating while stirring (1600 rpm). From 60° C. onwards, a consumption of hydrogen is observed, indicating the start of the hydrogenation reaction. After a contact time of 1 h 30 min, the autoclave is cooled using the cooling coil and by cutting the heating. The stirring is reduced to 250 rpm during the cooling. When the reactor reaches 30° C., the stirring is stopped and the autoclave is depressurized. The autoclave is opened and the reaction medium obtained is filtered through an 8 μm Millipore filter in order to separate the reaction medium from the solid catalyst, it being possible for the latter to be reused in another hydrogenation reaction.

A sample of the crude reaction product is withdrawn then analyzed by gas chromatography. A conversion of 100% is observed with a DHMF selectivity of 83.2%. This test corresponds to test no. 12 in table 1.

Example of the Synthesis of DHMF in the Presence of the Raney Nickel Bulk Catalyst In this test, use is made of:
a composition containing DFF (97.4% by weight of DFF and 2.6% by weight of FFCA): 10 g;
a Raney nickel bulk catalyst in an amount of 2% by weight of Ni with respect to the weight of DFF;
demineralized water: 400 ml.
Operating conditions:
reaction temperature: 100° C.;
hydrogen pressure: 50 bar;
initial pH of the reaction: 8.2;
reaction time: 1 h 00 min.

Introduced into a stainless steel autoclave having an internal capacity of 600 ml are: 10 g of a composition containing DFF, and the Raney nickel catalyst and also 400 ml of demineralized water. The pH is adjusted to 8.2. When the reactants have been placed in the autoclave, the latter is purged under nitrogen, then placed under 20 bar of hydrogen at the start of the heating while stirring (1600 rpm). From 60° C. onwards, a consumption of hydrogen is observed, indicating the start of the hydrogenation reaction. After a contact time of 1 h 00 min, the autoclave is cooled using the cooling coil and by cutting the heating. The stirring is reduced to 250 rpm during the cooling. When the reactor reaches 30° C., the stirring is stopped and the autoclave is depressurized. The autoclave is opened and the reaction medium obtained is filtered through an 8 μm Millipore filter in order to separate the reaction medium from the solid catalyst, it being possible for the latter to be reused in another hydrogenation reaction.

A sample of the crude reaction product is withdrawn then analyzed by gas chromatography. A conversion of 100% is observed with a DHMF selectivity of 60.1%.

This test corresponds to test no. 6 in table 1.

TABLE 1

| | Composition containing DFF | | | | Catalyst | | | | | | | |
|---|---|---|---|---|---|---|---|---|---|---|---|---|
| test no. | DFF content (%) | FFCA content (%) | Mass (g) | Solvent | Nature | wt % metal/ substrate | P H$_2$ (bar) | T (° C.) | Time | Conversion (%) | DHMF (%) | DHMTHF (%) |
| 1 | 93.1 | 6.9 | 10 | H$_2$O | Raney Ni | 2 | 50 | 95 | 1 h 00 | 100 | 39 | 25.9 |
| 2 | 99.2 | 0.8 | 10 | H$_2$O | Raney Ni | 2 | 10 | 65 | 1 h 30 | 100 | 46.8 | 2.7 |
| 3 | 99.2 | 0.8 | 4.5 | H$_2$O | Raney Ni | 2 | 50 | 60 | 1 h 00 | 100 | 34 | 30 |
| 4 | 99.2 | 0.8 | 4.5 | H$_2$O | Raney Ni | 2 | 100 | 60 | 1 h 00 | 100 | 55.2 | 14.8 |
| 5 | 97.4 | 2.6 | 30 | H$_2$O | Raney Ni | 1 | 100 | 50 | 1 h 15 | 100 | 42.8 | 0.4 |
| 6 | 97.4 | 2.6 | 10 | H$_2$O | Raney Ni | 2 | 100 | 50 | 1 h 00 | 100 | 60.1 | 18.2 |
| 7 | 97.4 | 2.6 | 10 | MeOH | Raney Ni | 2 | 100 | 60 | 1 h 00 | 100 | 43.4 | 0.5 |
| 8 | 97.4 | 2.6 | 10 | EtOH | Raney Ni | 2 | 100 | 60 | 1 h 00 | 100 | 19.7 | 0.7 |
| 9 | 99.2 | 0.8 | 20 | H$_2$O | Raney Ni | 2 | 100 | 60 | 1 h 30 | 100 | 35 | 28.7 |

TABLE 1-continued

| | Composition containing DFF | | | | Catalyst | | | | | | | |
|---|---|---|---|---|---|---|---|---|---|---|---|---|
| test no. | DFF content (%) | FFCA content (%) | Mass (g) | Solvent | Nature | wt % metal/ substrate | P H$_2$ (bar) | T (° C.) | Time | Conversion (%) | DHMF (%) | DHMTHF (%) |
| 10 | 93.1 | 6.9 | 9 | H$_2$O | 5% Pd/C | 0.2 | 50 | 120 | 1 h 15 | 100 | 0 | 78.9 |
| 11 | 97.4 | 2.6 | 10 | H$_2$O | 5% Pd/C | 0.2 | 20 | 65 | 0 h 15 | 100 | 0 | 69.4 |
| 12 | 99.2 | 0.8 | 10 | H$_2$O | 5% Pd/C | 0.2 | 20 | 70 | 1 h 10 | 100 | 83.2 | 4.9 |
| 13 | 97.4 | 2.6 | 10 | H$_2$O | 5% Pd/C | 0.2 | 20 | 65 | 0 h 15 | 100 | 0 | 73.4 |
| 14 | 97.4 | 2.6 | 9 | MeOH | 5% Pd/C | 0.2 | 20 | 45 | 0 h 15 | 100 | 0 | 70.6 |
| 15 | 97.4 | 2.6 | 9 | EtOH | 5% Pd/C | | 20 | 45 | 0 h 20 | 100 | 0 | 74.7 |

All of the other tests, nos. 1 to 8, 10 and 12 to 14, were carried out in the same manner as described above, while varying the nature and amount of catalyst, the solvent, the pH, the temperature, the molecular hydrogen pressure and the reaction time. All the results obtained appear in table 1.

This table demonstrates the very advantage of the process that is the subject of the present invention: it is thus possible, working at low temperatures and under moderate pressures, with low doses of catalyst, to selectively obtain DHMF and DHMTHF.

The invention claimed is:

1. A process for synthesizing 2,5-di(hydroxymethyl)furan DHMF) and/or 2,5-di (hydroxymethyl) tetrahydrofuran DHMTHF, by bringing into contact:
   a) a composition containing furan-2,5-dialdehyde (DFF),
   b) a protic solvent,
   c) a source of hydrogen,
   d) and a hydrogenation catalyst,
wherein the composition a) is derived from the oxidation of 5-hydroxymethyl furaldehyde (5-HMF) in the presence of at least an organic acid, a nitroxyl radical, a source of oxygen and an oxygen transfer agent.

2. The process as claimed in claim 1, wherein the composition a) has a content of DFF by weight at least equal to 90%.

3. The process as claimed in claim 1, wherein the protic solvent b) is selected from the group consisting of water, methanol, ethanol, isopropanol, 1-propanol, 1-butanol and the mixtures of these solvents.

4. The process as claimed in claim 1, wherein the synthesis reaction via hydrogenation takes place at a temperature between 30° C. and 180° C.

5. The process as claimed in claim 1, wherein the source of hydrogen c) is molecular hydrogen, under a pressure of between 1 bar and 400 bar.

6. The process as claimed in claim 1, wherein the hydrogenation catalyst is selected from metal catalysts of bulk or supported type, based on Ni, Cu, Fe, Pd, Rh, Ir, Ru, Co, or Pt.

7. The process as claimed in claim 6, wherein the support for the supported catalyst is selected from the group consisting of activated carbon, silica, alumina, mixtures of silica and alumina, oxides of titanium, zirconium, magnesium and cerium, and mixed oxides based on Si, Al, Ti and Zr, and the metal content represents from 0.1% to 90% of the total weight of the catalyst.

8. The process as claimed in claim 1, wherein the contact time between the various constituents a), b), c) and d) is between 1 minute and 8 hours.

9. The process as claimed in claim 1, wherein the process is carried out in a fixed bed or batch reactor that is pressurized or unpressurized.

10. The process as claimed in claim 9, wherein the amount of catalyst is between 0.01% and 30% with respect to the weight of DFF, in the case of a batch reactor.

* * * * *